(12) United States Patent
Perricone

(10) Patent No.: US 6,296,861 B1
(45) Date of Patent: Oct. 2, 2001

(54) TREATMENT OF SKIN DAMAGE USING CONJUGATED LINOLEIC ACID AND ASCORBYL FATTY ACID ESTERS

(76) Inventor: Nicholas V. Perricone, 27 Coginchaug Ct., Guilford, CT (US) 06437

(*) Notice: Subject to any disclaimer, the term of this patent is extended or adjusted under 35 U.S.C. 154(b) by 0 days.

(21) Appl. No.: 09/563,169

(22) Filed: May 2, 2000

Related U.S. Application Data

(60) Provisional application No. 60/132,282, filed on May 3, 1999.

(51) Int. Cl.[7] .................................................. A61K 7/00
(52) U.S. Cl. ............................................ 424/401; 514/557
(58) Field of Search ............................. 514/557; 424/401

(56) References Cited

U.S. PATENT DOCUMENTS

| | | |
|---|---|---|
| 4,393,043 | 7/1983 | Koulbanis et al. . |
| 5,545,398 | 8/1996 | Perricone . |
| 5,554,647 | 9/1996 | Perricone . |
| 5,574,063 | 11/1996 | Perricone . |
| 5,709,868 * | 1/1998 | Perricone .............................. 424/401 |

FOREIGN PATENT DOCUMENTS

WO 00/37040 * 6/2000 (WO) .

OTHER PUBLICATIONS

Allen, R.G., et al., J. Biol. Chem. 272:24805–24812 (1997).
Dubertret, L., Skin News editorial, 60th Annual Meeting of the Society for Investigative Dermatology, May 5–9, 1999.
Ibbotson, S.H., J. Invest. Dermatol. 112:933–938 (1999).
Life Extension, Apr. 1999 abstracts of Cancer Lett. 27:15–22 (1998) and Biochem. Biophys. Res. Commun. 244:678–682 (1998).

* cited by examiner

*Primary Examiner*—Michael A. Williamson
(74) *Attorney, Agent, or Firm*—Mary M. Krinsky

(57) ABSTRACT

A synergistic combination of conjugated linoleic acid and fatty acid esters of ascorbic acid is topically applied to treat skin damage, such as contact dermatitis, atopic dermatitis, xerosis, eczema, rosacea, seborrhea, psoriasis, thermal and radiation burns, other types of skin inflammation, and aging. Typical compositions contain from about 1% to about 25% by weight of a CLA preparation containing 9,11-octadecadienoic acid and 10,12-octadecadienoic acid, and from about 0.5% to about 15% by weight of a saturated fatty acid ester of ascorbic acid such as ascorbyl palmitate.

17 Claims, No Drawings

TREATMENT OF SKIN DAMAGE USING CONJUGATED LINOLEIC ACID AND ASCORBYL FATTY ACID ESTERS

CROSS-REFERENCES TO RELATED APPLICATIONS

This application claims priority benefit of U.S. application serial No. 60/132,282, filed May 3, 1999.

BACKGROUND OF THE INVENTION

1. Field of the Invention

This invention relates to the topical application of conjugated linoleic acid together with fatty acid esters of ascorbic acid for the treatment of acute and chronic skin damage. Therapies according to the invention are particularly efficacious for treating a variety of skin conditions including contact dermatitis (particularly diaper area dermatitis), atopic dermatitis, xerosis, eczema, rosacea, seborrhea, psoriasis, thermal and radiation burns, other types of skin inflammation, and the tissue degenerative effects of aging.

2. Description of Related Art

Skin inflammation and aging are closely related phenomena. So similar are the processes involved with both, that aging is sometimes described dermatologically as a chronic low grade inflammatory condition. In acute inflammation, there is typically a respiratory burst of neutrophil activity that initiates cascades that typically involve a change in the oxidation state of the cell. Acute inflammation is also characterized by mast cell degranulation wherein serotonin is produced, which acts as a signal transduction factor. Following that, excited oxygen species are generated, e.g., superoxide anion, and these damage the lipid-rich membranes and activate the chemical mediators of proinflammation and inflammation.

Alteration in the redox state of the cell activates transcription factors such as NFκB as well as AP1, which then causes production of proinflammation mediators. These mediators, such as TFα and various interleukins, cause a burst of cytokines. Arachadonic acid is released, which is oxidized to biologically active mediators. When arachadonic acid is oxidized via the cyclooxygenase or lipoxygenase pathways, for example, prostaglandins, leukotrines, and hyroxyeicosatetraenoic acid (HETE) are produced, which cause erythma, edema, and free radical production. Transcription factors such as NFκB and AP1alter DNA expression in the cell and produce cytokines and proteinases such as collagenase.

Similar metabolic events are observed in skin aging. Cell age is due in part to free radical damage, which takes place mostly within the cell membrane. The cell membrane is most susceptible to attack by free radicals because of its dense molecular structure largely comprising lipids and lipoproteins, which are easily oxidized by reactive oxygen species. In-skin, reactive oxygen species such as singlet oxygen, the superoxide anion, and hydroxyl radicals, as well as other free radicals, are generated in normal metabolism, as well as through ultraviolet sun exposure, other forms of radiation, other environmental factors such as pollution or exposure to chemicals in the home or workplace, and the like, active in the arachidonic acid cascade. As in inflammation, free radicals activate chemical mediators that produce prostaglandins and/or leukotrines.

The body contains an endogenous antioxidant defense system made up of antioxidants such as vitamins C and E, glutathione, and enzymes, e.g., superoxide dismutase. When metabolism increases or the body is subjected to other stress such as infection, extreme exercise, radiation (ionizing and non-ionizing), or chemicals, the endogenous antioxidant systems are overwhelmed, and free radical damage takes place. Over the years, the cell membrane continually receives damage from reactive oxygen species and other free radicals, resulting in cross-linkage or cleavage or proteins and lipoprotins, and oxidation of membrane lipids and lipoproteins. Damage to the cell membrane can result in myriad changes including loss of cell permeability, increased intercellular ionic concentration, and decreased cellular capacity to excrete or detoxify waste products. As the intercellular ionic concentration of potassium increases, colloid density increases and m-RNA and protein synthesis are hampered, resulting in decreased cellular repair. Some cells become so dehydrated they cannot function at all.

In skin aging, the regularity of tissue structure is lost. Individual cells enlarge, but the total number of cells decreases approximately 30%. Intercellular collagen increases, and the proportion of soluble collagen decreases. Cross-linking between long-chain collagen macromolecules occurs. Elastin loses its discrete structure and elasticity, and has an increased calcium content. The dermis microscars and diminishes.

Sunlight and chemical exposure wreaks far greater destruction on the skin than time itself, and intensifies and augments the aging process. There is substantial evidence that ultraviolet radiation induces the formation of reactive oxygen species which are implicated as toxic intermediates in the pathogenesis of photoaging (Ibbotson, S. H., et al., *J. Investig. Derm.* 112: 933–938 (1999)). Activation of transcription factors such as AP1 causes gene expression of collagenases which cause further damage. Free radical damage to the surface of the skin from sun and chemical exposure is manifested as lines, mottling, discoloration, precancers and cancers. Aging of both skin and other tissues is, in part, the result of constant free radical damage to cell membranes, leading to decreased cell function. This results in accumulation of waste products in the cells, such as lipofuscin; increase in the potassium content of the cells, which results in dehydration of the cells; and decreased production of messenger RNA and proteins.

Early suggestions for dealing with aging effects in skin were predominantly aimed at lubrications and emollients through use of topical compositions containing soothing agents, e.g., as exemplified by commercial hand lotion products and the like. More recently, attention has been directed to agents which address the underlying processes involved in skin damage, such as the free radical generation processes (N.V. Perricone, *The Wrinkle Cure*, Rodale Press, Emmaus, Pa., 2000). In this regard, investigations have been made with respect to the antioxidants vitamin E and vitamin C to quench free radicals on the surface of the skin and to protect lipid membranes intracellularly (Wilson, R., *Drug and Cosmetic Industry*, 32–34, 38, and 68, August 1992).

It would be desirable to have alternative topical compositions for skin damage, particularly compositions that are efficient in free radical scavenging in membranes.

BRIEF SUMMARY OF THE INVENTION

It is an objective of the invention to provide new compositions and methods for the treatment of skin damage, such as atopic dermatitis, contact dermatitis (particularly diaper area dermatitis), xerosis, eczema, rosacea, seborrhea, psoriasis, thermal and radiation burns, other types of skin inflammation, and aging.

These and other objectives of the invention are accomplished by the present invention, which provides a combination of conjugated linoleic acid with fatty acid esters of ascorbic acid, which are topically applied to exposed or affected skin areas, primarily for the treatment but also for the prevention of skin damage, often in association with a dermatologically acceptable carrier. The amount of active ingredients necessary to treat damaged skin is not fixed per se, and necessarily is dependent upon the isomers of conjugated linoleic acid and identity of the ascorbyl esters employed, the proportions of the two active ingredients, the amount and type of any adjunct ingredients employed in the composition with the active ingredients, the user's skin type, and the severity, extent, and nature of the dermatological problem treated. In some typical embodiments, the composition contains from about 1% to about 25%, more narrowly from about 5% to about 15% by weight, conjugated linoleic acid, and from about 0.5% to about 15%, more narrowly from about 3% to 10% by weight ascorbyl palmitate.

DETAILED DESCRIPTION OF THE INVENTION

In the practice of the invention, a synergistic combination of conjugated linoleic acid and fatty acid esters of ascorbic acid are used to treat skin damage when topically applied in effective amounts.

Any synthetic or natural conjugated linoleic acid (herein sometimes referred to as "CLA"), alone or in combination with linoleic and linolenic acid found in many essential fatty acid mixtures, and/or biological equivalent derivatives and isomers thereof, may be employed as one of the active ingredients in compositions of the invention. By "linoleic acid" is meant 9,12-octadecadienoic acid. (See the *Merck Index*, 11th ed., 1989, entry 5382.) "Conjugated linoleic acid" are linoleic isomers having the double bonds separated by a single bond. Conjugated linoleic acids are a large family of molecules including, but not limited to, 9,11-octadecadienoic acid of the formula $CH_3-(CH_2)_5-CH=CH-CH=CH-(CH_2)_7-COOH$, and its stereoisomers, and 10,12-octadecadienoic acid of the formula $CH_3-(CH_2)_4-CH=CH-CH=CH-(CH_2)_8-COOH$ and its stereoisomers, as well as the less common dienoic CLAs and eleostearic acid (9,11,13-octadecatrienoic acid having the formula $CH_3-(CH_2)_3-CH=CH-CH=CH=CH-(CH_2)_7-COOH$ and its stereoisomers. Since these unsaturated molecules contain double bonds, there are a number of geometric isomers containing either cis or trans double-bonds, or both. Such as forms are sometimes denoted as as cis-9, cis-11, and so on. As used herein, CLA specifically includes natural forms wherein the bonds are typically are all cis, as well as forms chemically or biologically modified to contain a mixture of both cis and trans double bonds and those all trans, as well as polymerized forms exhibiting the same biological activity (ibid., entry 5383), and isomers thereof.

CLA can be chemically prepared and is available commercially as various reagent grade octadecadienoic acids and as more economical preparations containing some impurities, e.g., from Hercules, Inc., in Wilmington DE, and marketed under the tradename Palmolyn (RTM) 380™, a preparation that contains about 69% active ingredient. Since linoleic acid is a natural constituent of many natural vegetable and marine oils, typically present as a triglyceride substitutent, natural oils can provide active ingredients of the invention or precursors in some embodiments. Thus, encompassed by the invention are oils containing high amounts of linoleic acid such as cottonseed, soybean, peanut, corn, sunflower, safflower, poppy seed, linseed, canola, perilla and certain fish oils, as well as these and other oils enriched with linoleic acid, such as those produced by high-linoleic soybean, sunflower and safflower oil varieties, as well as oils chemically enriched with linoleic acid such as transesterified or interesterified oils of all types, which can be modified to obtain CLA. It is an advantage of the invention that even oils containing relatively low amounts of linoleic acid such as coconut, palm, and palm kernel oil, many of which are quite inexpensive, can be interesterified with oils high in linoleic acid content such as those listed above to obtain linoleic-enriched oils, and that any oil can be transesterified with linoleic acid, or reacted with CLA anhydride, to provide other linoleic-enriched oils, and these chemically modified feedstocks can be engineered to contain conjugated linoleic acid isomers. Natural preparations are preferred in some embodiments because they exhibit desirable physical characteristics and are nontoxic.

Also encompassed by the invention are derivatives of CLA exhibiting similar biological properties such as CLA esters (e.g., commercially available methyl, ethyl, and propyl esters), CLA chlorides, and CLA salts (e.g., sodium salts, but particularly zinc salts shown to have special efficacy in the treatment of skin disorders; see PCT/GB97/02854, published internationally as WO 98/17269 on Apr. 30, 1998). For convenience, where the term "conjugated linoleic acid" is employed herein, it includes all isomers of the free acid and structurally related, biologically equivalent derivatives such as salts and esters.

Fatty acid esters of ascorbic acid include ascorbic acid acylated with single or multiple fatty acid groups, wherein the fatty acids typically have 8 to 24 carbon atoms, and their salts. The more oxidation-resistant saturated fatty acid esters of ascorbic acid are preferred, including, but not limited to, ascorbyl laurate, ascorbyl myristate, ascorbyl palmitate, ascorbyl stearate, and ascorbyl behenate, and their salts, e.g., magnesium ascorbyl stearate. Ascorbyl palmitate is used in one preferred embodiment. As denoted herein, where fatty acid esters are described, e.g., ascorbyl stearate, compositions having predominantly that ester, e.g., predominantly stearate, are included. The esters may be prepared using hydrogenated oils or fats, or fractions thereof, and contain small amounts of another ester. Ascorbyl stearate prepared using canola, for example, commonly contain about 4% ascorbyl palmitate.

Both CLA and ascorbyl fatty acid esters are fat-soluble. Therefore, preparations containing both active ingredients can be applied neat to skin tissue. It is an advantage of the invention that the active compound is fatty so that it physically contributes to the lubrication of affected skin areas to which it is applied.

However, only effective amounts of both are needed to treat skin damage (including either inflammation or aging or both), so generally topical application to exposed or affected skin sites is accomplished in association with a carrier, and particularly one in which the CLA and ascorbyl ester active ingredients are soluble per se or is effectively solubilized (e.g., as an emulsion or microemulsion). By "effective amount" is meant an amount of both active ingredients sufficient to stabilize the cell plasma membrane by scavenging and neutralizing free radicals and exhibiting antioxidant activity, thereby inhibiting the arachidonic acid cascade which leads to the activation of transcription factors that direct the cell nucleus into producing pro-inflammatory chemicals such as arachidonic acid. In the practice of the invention, active ingredients are typically delivered to lipid-rich layers of the skin in amounts effective to prevent inflammation and accelerate collagen synthesis.

Where employed, the carrier is inert in the sense of not bringing about a deactivation or oxidation of the either ingredient, particularly CLA, and in the sense of not bringing about any adverse effect on the skin areas to which it is applied. In one preferred practice of the invention, the combination is applied in admixture with a dermatologically acceptable carrier or vehicle (e.g., as a lotion, cream, ointment, soap, stick, or the like) so as to facilitate topical application and, in some cases, provide additional therapeutic effects as might be brought about, e.g., by moisturizing of the affected skin areas. While the carrier for the active ingredients in dermatological compositions can consist of a relatively simple solvent or dispersant such as water, it is generally preferred that the carrier comprise a composition more conducive to topical application, and particularly one which will form a film or layer on the skin to which it is applied so as to localize the application and provide some resistance to washing off by immersion in water or by perspiration and/or aid in the percutaneous delivery of the active agent. Many preparations are known in the art, and include lotions containing oils and/or alcohols and emollients such as hydrocarbon oils and waxes, silicone oils, vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids. One preferred embodiment is an oil-in-water cream. Such compositions are referred to herein as dermally or dermatologically acceptable carriers.

Suitable carriers include water, alcohols, oils and the like, chosen for their ability to dissolve or disperse both ingredients and any other ingredients used in the treatment. Generally, even low concentrations of active ingredients in a carrier are suitable, depending upon the application regimen and adjunct ingredients employed. As summarized above, many embodiments contain from about 1% to about 25% by weight, more narrowly from about 3 to 5% to about 11 to 15%, by weight CLA, and from about 0.5% to about 15%, more narrowly from about 3% to about 7 to 10% by weight, ascorbyl palmitate. Chronic conditions typically require a lower concentration of active ingredients than do acute conditions. As a practical matter, however, to avoid the need for repeated application, it is desirable that the topically applied composition (i.e., PPC plus carrier) be formulated to contain at least about 1% by weight CLA, and many embodiments contain more than 1 weight % CLA, and at least about 1% ascorbyl palmitate, again with many embodiments containing more than 1% by weight. One efficacious embodiment contains from about 3% to about 10% by weight CLA, and from about 2% to about 7% ascorbyl palmitate.

Generally in the practice of methods of the invention, the composition is topically applied to the affected skin areas in a predetermined or as-needed regimen either at intervals by application of a lotion or the like, it generally being the case that gradual improvement is noted with each successive application. Insofar as has been determined based upon clinical studies to date, no adverse side effects are encountered.

Some embodiments of this invention contain at least one other adjunct ingredient in addition to CLA and an ascorbyl ester. Adjunct ingredients include, but are not limited to, α-hydroxy acids. Many embodiments employ more than one adjunct ingredient. As used herein, the term "a-hydroxy acid" has reference to and encompasses the general class of organic compounds containing at least one hydroxy group and at least one carboxyl group, and wherein at least one hydroxyl group is located on the α-carbon atom. Typically, the compounds are organic acids having at least one carboxylic acid group and at least one hydroxyl group on the α-carbon atom, and may contain other functional groups including additional hydroxyl and carboxylic acid moieties. Preferred α-hydroxy acids and/or α-hydroxy acid derivatives are less bulky structurally so that they penetrate the skin well, and thus have a backbone of from one to three carbon atoms such as those set out in U.S. Pat. No. 5,965,618 at column 6 lines 4 to 29. Where employed, glycolic and/or lactic acid or their derivatives are preferred; glycolic acid is especially efficacious.

While not wishing to be bound to any theory, it is possible that the synergistic combination of conjugated linoleic acid with ascorbyl fatty acid esters is efficacious in the treatment of skin damage because it is fat-soluble and readily disperses in cell membranes and other cellular components. Both active ingredients readily penetrate skin. CLA has been previously suggested in skin compositions in combination with jojoba (U.S. Pat. No. 4,393,043 to Koulbanis, et al.) It may be that the combination acts as an especially active free radical scavenger and neutralizer, and prevents the cross-linking of cell membranes that is often seen in its post-inflammatory phases. By the same token, CLA and ascorbyl ester modulation of free radicals and other oxidative species appears to affect gene expression, including expression of nuclear factor κ-B (NF-κB), nitric oxide synthetase and other mediators at all stages of proinflammation and inflammation. Alteration of lipid peroxidation, protein cross-linking, growth factor stimulation, and membrane permeability may explain the negative effect on the symptoms of damaged skin.

When skin is inflamed from ultraviolet radiation, irritants, trauma, and other reasons, phospholipase-A-2 produces arachidonic acid from the phospholipid-rich membranes of the cell, resulting in the production of metabolites. We now know that stabilization of the cell membrane can inhibit the inflammatory cascade, therefore preventing the inflammatory response. It is also now known that arachidonic acid has a direct toxic effect on the mitochondria, resulting in the uncoupling of oxidative phosphorylation, resulting in free radical damage to the mitochondrial membrane, CLA and ascorbyl esters appear to intersperse in the cell membrane, stabilizing the membrane, and, at the same time, providing antioxidant capability. In addition, the incorporation of CLA into the cell membrane appears to enhance membrane activity, such as exchange of nutrients and wastes of the cellular environment. This also enhances cellular function and repair.

Methods and compositions of the present invention are particularly useful for treating damaged skin tissue, particularly various types of dermatitis, skin conditions such as rosacea, seborrhea, eczema, xerosis (dry skin), psoriasis, thermal and radiation burns, and other types of inflammation. Compositions of the invention are useful in treating both contact dermatitis and atopic dermatitis. Topical application of CLA and ascorbyl fatty acid esters according to the invention can also be effective to prevent symptoms in aging persons for the inhibition of microscarring of the dermis and to promote collagen production. It is an advantage of the invention that topical application of CLA with ascorbyl esters provides a simple, non-invasive, nontoxic, over-the-counter topical method for treating all kinds of skin damage, including aging.

All references cited herein are hereby incorporated by reference, as are additional ingredients and methods set out in U.S. Pat. Nos. 4,775,530, 5,376,361, 5,409,693, 5,545,398, 5,574,063, 5,643,586, 5,709,868, 5,879,690, 5,965,618, 5,968,618, and 6,051,244. Generally, these compositions contain other active ingredients summarized above that enhance the effect of active ingredients of the invention.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the invention in any sequence which is effective to meet the objectives there intended, unless the context specifically indicates the contrary.

What is claimed is:

1. A method for the treatment of skin damage selected from the group consisting of inflammation, eczema, atopic dermatitis, contact dermatitis, seborrhea, xerosis, rosacea, thermal or radiation burns, and psoriasis, comprising topically applying to the skin areas subject to such damage a composition containing an effective amount of two active ingredients: a conjugated linoleic acid and a fatty acid ester of ascorbic acid.

2. A method according to claim 1 wherein the conjugated linoleic acid component comprises a mixture of 9,11-octadecadienoic acid and 10,12-octadecadienoic acid.

3. A method according to claim 1 wherein the fatty acid ester of ascorbic acid is saturated.

4. A method according to claim 3 wherein the fatty acid ester of ascorbic acid is selected from the group consisting of ascorbyl laurate, ascorbyl myristate, ascorbyl palmitate, ascorbyl stearate, ascorbyl behenate, and mixtures thereof.

5. A method according to claim 4 wherein the fatty acid ester of ascorbic acid is ascorbyl palmitate.

6. A method according to claim 1 wherein the composition comprises a mixture of from about 1% to about 25% by weight conjugated linoleic acid, and from about 0.5% to about 15% by weight ascorbyl palmitate.

7. A method according to claim 6 wherein the composition comprises a mixture of about 5% to about 15% by weight conjugated linoleic acid, and from about 3% to about 10% by weight ascorbyl palmitate.

8. A method according to claim 1 wherein the skin damage is inflammation.

9. A method according to claim 1 wherein the conjugated linoleic acid is derived from a natural oil.

10. A method according to claim 9 wherein the natural oil is linoleic-enriched.

11. A method according to claim 1 wherein the composition further comprises an α-hydroxy acid.

12. A method according to claim 11 wherein the α-hydroxy acid is glycolic acid.

13. A method for the treatment of skin damage selected from the group consisting of inflammation, eczema, atopic dermatitis, contact dermatitis, seborrhea, xerosis, rosacea, thermal or radiation burns, and psoriasis, comprising topically applying to the skin areas subject to such damage a compostion containing from about 1% to about 15% by weight of a conjugated linoleic active ingredient containing 9,1-octadecadienoic acid and 10,12-octadecadienoic acid, and from about 0.5% to about 10% by weight ascorbyl palmitate.

14. A method according to claim 13 wherein the skin damage is inflammation.

15. A method according to claim 13 wherein the composition contains from about 3% to about 11% conjugated linoleic acid and from about 3% to about 7% ascorbyl palmitate.

16. A method according to claim 13 wherein the composition further contains glycolic acid.

17. A method according to claim 13 wherein the conjugated linoleic acid is obtained from a natural oil.

\* \* \* \* \*